United States Patent
Das et al.

(10) Patent No.: US 9,271,688 B2
(45) Date of Patent: Mar. 1, 2016

(54) SYSTEM AND METHOD FOR CONTRAST AGENT ESTIMATION IN X-RAY IMAGING

(75) Inventors: Bipul Das, Bangalore (IN); Ajay Narayanan, Bangalore (IN); Pratik Shah, Bangalore (IN)

(73) Assignee: GENERAL ELECTRIC COMPANY, Niskayuna, NY (US)

(*) Notice: Subject to any disclaimer, the term of this patent is extended or adjusted under 35 U.S.C. 154(b) by 293 days.

(21) Appl. No.: 13/433,055

(22) Filed: Mar. 28, 2012

(65) Prior Publication Data
US 2013/0261441 A1    Oct. 3, 2013

(51) Int. Cl.
*A61B 6/00* (2006.01)
*G06T 5/50* (2006.01)
*A61B 6/03* (2006.01)

(52) U.S. Cl.
CPC .......... *A61B 6/481* (2013.01); *A61B 6/482* (2013.01); *A61B 6/507* (2013.01); *A61B 6/5217* (2013.01); *G06T 5/50* (2013.01); *A61B 6/032* (2013.01); *G06T 2207/10116* (2013.01); *G06T 2207/20224* (2013.01); *G06T 2207/30101* (2013.01)

(58) Field of Classification Search
CPC ...... A61B 6/481; A61B 6/482; A61B 6/5217; A61B 6/507; A61B 6/032; G06T 5/50; G06T 2207/10116; G06T 2207/20224; G06T 2207/30101
See application file for complete search history.

(56) References Cited

U.S. PATENT DOCUMENTS

| 6,236,706 | B1 | 5/2001 | Hsieh |
| 6,891,918 | B2 | 5/2005 | Drummond et al. |
| 7,627,080 | B2 | 12/2009 | Proksa |
| 7,756,239 | B2 | 7/2010 | Wu et al. |
| 7,778,454 | B2 * | 8/2010 | Grasruck et al. ............. 382/128 |
| 7,852,986 | B2 | 12/2010 | Loef et al. |

(Continued)

FOREIGN PATENT DOCUMENTS

WO    WO 2012/015285 A2 *    2/2012

OTHER PUBLICATIONS

Shechter et al., "Accurate material quantification in dual energy CT" Proc. SPIE 8313, Medical Imaging 2012: Physics of Medical Imaging, 83132Z. (Conference: Feb. 2, 2012, San Diego, CA).*

(Continued)

*Primary Examiner* — Long V Le
*Assistant Examiner* — Colin T Sakamoto
(74) *Attorney, Agent, or Firm* — Fletcher Yoder, P.C.

(57) ABSTRACT

The disclosed embodiments relate to determining an amount of a contrast agent in an image. For example, a computer-implemented method of image processing includes generating, from a first polychromatic contrast-enhanced X-ray image obtained at a first energy and a second polychromatic contrast-enhanced X-ray image obtained at a second energy, a simulated first monochromatic contrast-enhanced X-ray image and a simulated second monochromatic contrast-enhanced X-ray image. The simulated first monochromatic contrast-enhanced X-ray image includes first regions of enhanced contrast and the simulated second monochromatic contrast-enhanced includes second regions of enhanced contrast. The method also includes isolating the first and second regions of enhanced contrast from other regions of the image, and determining an amount of the contrast agent within the first and second regions of enhanced contrast based at least on a derived partial signal attributable to the contrast agent.

12 Claims, 6 Drawing Sheets

(56) References Cited

U.S. PATENT DOCUMENTS

| | | | |
|---|---|---|---|
| 2006/0067473 A1* | 3/2006 | Eberhard et al. | 378/98.9 |
| 2010/0111398 A1 | 5/2010 | Mitra et al. | |
| 2011/0188720 A1 | 8/2011 | Narayanan et al. | |
| 2011/0229003 A1 | 9/2011 | Yang | |
| 2012/0045109 A1* | 2/2012 | Proksa et al. | 382/131 |

OTHER PUBLICATIONS

Yu et al., "Virtual monochromatic imaging in dual-source dual-energy CT: Radiation dose and image quality". Med. Phys. 38 (12) Dec. 2011. pp. 6371-6379. (published online Nov. 9, 2011).*

Goodsitt et al., "Accuracies of the synthesized monochromatic CT numbers and effective atomic numbers obtained with a rapid kVp switching dual energy CT scanner" Med. Phys. 38 (4), Apr. 2011, pp. 2222-2232.*

Medonça et al., "Multi-Material Decomposition of Spectral CT Images" Proc. SPIE 7622, Medical Imaging 2010: Physics of Medical Imaging, 76221W Mar. 22, 2010.*

Vinegar et al., "Tomographic imaging of three-phase flow experiments" Rev. Sci. Instrum. 58 (1), Jan. 1987 pp. 96-107.*

Liu et al., "Quantitative imaging of element composition and mass fraction using dual-energy CT: Three-material decomposition" Med. Phys. 36 (5), May 2009 pp. 1602-1609.*

Brendel, B. et al.; "A novel CT perfusion protocol for quantitative contrast material mapping", IEEE Nuclear Science Symposium, Oct. 24-Nov. 1, 2009, pp. 3021-3025.

de Vries, Anke, et al.; "Biodistribution of a radiolabeled CT contrast agent quantified by dual modality SPECT and spectral CT". Nanoparticle Probes III, Sep. 26, 2009, 2 pages.

Stenner, P., et al.; "Dynamic iterative beam hardening correction (DIBHC) for an optimized assessment of cardiac perfusion in ECG-correlated CT", IEEE Nuclear Science Symposium, Oct. 24-Nov. 1, 2009, pp. 3523-3530.

"High-resolution pre-clinical K-edge CT imaging", 6th Philips MDCT Users Meeting, May 10, 2009, 3 pages.

* cited by examiner

SYSTEM AND METHOD FOR CONTRAST AGENT ESTIMATION IN X-RAY IMAGING

BACKGROUND

In computed tomography (CT) and fluoroscopy imaging systems, X-ray radiation spans a subject of interest, such as a human patient, and a portion of the radiation impacts a detector or a photographic plate where the image data is collected. In some X-ray systems the photographic plate is then developed to produce an image, which may be used by a radiologist or attending physician for diagnostic purposes. In digital X-ray systems a photo detector produces signals representative of the amount or intensity of radiation impacting discrete pixel regions of a detector surface. The signals may then be processed to generate an image that may be displayed for review. In CT systems a detector array, including a series of detector elements, produces similar signals through various positions as a gantry is displaced around a patient.

In the images produced by such systems, contrast is created based upon the varying attenuation of the X-rays by the materials encountered as the X-rays penetrate the patient's tissue. Typically, materials having atoms with a greater atomic number will have a greater attenuation of X-rays. Thus, tissues such as bone may create relatively high contrast within an image compared to other tissues, such as fatty tissue. Some techniques used for CT and fluoroscopy imaging use a contrast agent to artificially create contrast within an area that would typically not have relatively high contrast, such as blood vessels. The contrast agents may include one or more atoms capable of attenuating X-rays with a relatively high degree of efficiency, such as iodine. For example, in CT angiography, a contrast agent is typically injected into the patient, followed by CT imaging. The contrast agent typically perfuses through certain tissues of the patient, and the resulting CT images contain regions of enhanced contrast corresponding to the areas that are perfused with the contrast agent.

Contrast agents may include ionic or non-ionic, organic compounds. Contrast agents that utilize iodine typically include water-soluble organic compounds based on their relatively low toxicity and their covalent bonding of iodine atoms. Thus, in addition to the iodine atoms, such contrast agents include carbon (C), hydrogen (H), and may include nitrogen (N), oxygen (O) and other atoms having relatively low X-ray attenuating properties. Accordingly, the proportion of these atoms to iodine atoms may affect the signal response of the contrast agent to the X-rays. Thus, the use of different contrast agents may lead to varying signal responses based at least on the molecular structure of the contrast agent.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a computer-implemented method of image processing is provided. The method includes generating, from a first polychromatic contrast-enhanced X-ray image obtained at a first energy and a second polychromatic contrast-enhanced X-ray image obtained at a second energy, a simulated first monochromatic contrast-enhanced X-ray image and a simulated second monochromatic contrast-enhanced X-ray image. The simulated first monochromatic contrast-enhanced X-ray image includes first regions of enhanced contrast and the simulated second monochromatic contrast-enhanced includes second regions of enhanced contrast. The method also includes isolating the first and second regions of enhanced contrast from other regions of the image, and determining an amount of the contrast agent within the first and second regions of enhanced contrast based at least on a derived partial signal attributable to the contrast agent.

In another embodiment, a computer-implemented method of image processing is provided. The method includes isolating, in a polychromatic contrast-enhanced X-ray image of a patient comprising regions of enhanced contrast, the regions of enhanced contrast from other regions of the image. The regions of enhanced contrast include a partial signal attributable to a contrast agent. The method also includes determining a volume of the contrast agent within a given volume of the regions of enhanced contrast using a composite linear attenuation coefficient for the contrast agent and a polychromatic spectral response of the given volume. The composite linear attenuation coefficient for the contrast agent includes a weighted sum of the respective linear attenuation coefficients for the contrast agent over a range of energies used to obtain the polychromatic contrast-enhanced X-ray image.

In a further embodiment, a system is provided. The system includes a processor configured to execute a set of instructions stored within a memory to process a contrast-enhanced X-ray image and the memory having the set of instructions. The set of instructions are executable by the processor to generate, from a first polychromatic contrast-enhanced X-ray image obtained at a first energy and a second polychromatic contrast-enhanced X-ray image obtained at a second energy, a simulated first monochromatic contrast-enhanced X-ray image and a simulated second monochromatic contrast-enhanced X-ray image. The simulated first monochromatic contrast-enhanced X-ray image is simulated at the first energy and includes first regions of enhanced contrast and the simulated second monochromatic contrast-enhanced X-ray image is simulated at the second energy and includes second regions of enhanced contrast. The set of instructions are also executable by the processor to and determine an amount of a contrast agent within the first and second regions of enhanced contrast based at least on a relationship between a volume of the contrast agent within a given volume of the simulated first and second monochromatic contrast-enhanced X-ray images and the respective spectral responses of the simulated first and second monochromatic contrast-enhanced X-ray images.

BRIEF DESCRIPTION OF THE DRAWINGS

These and other features and aspects of embodiments of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Certain imaging methods, such as CT perfusion studies, attempt to measure blood flow through various patient tissues by injecting a contrast agent into the patient's bloodstream. As the contrast agent enters a given tissue, the tissue will exhibit enhanced contrast in an X-ray (e.g., CT) image. This enhanced contrast may be tracked by the imaging system and can provide insight into a tissue's ability to uptake a flow of blood over time, which may have diagnostic value. While such methods can provide qualitative information regarding relative uptake rates between tissues, it may be desirable to quantify an amount of the contrast agent with a given volume of enhanced contrast tissue. For example, such quantification may enable more direct comparisons between image acquisitions and between contrast agents. Unfortunately, as noted above, different contrast agents may produce different signal responses. For example, the ratio of a highly attenuating atom (e.g., iodine) to other relatively low attenuation atoms may vary across different contrast agents. Therefore, equal weight or volume-based doses of contrast agents may not result in similar contrast enhancement.

While the signal resulting from various contrast agents may be different, it is now recognized that it may be possible to model the signal response of a contrast agent based on its attenuation coefficient at particular energies used for imaging. For example, in accordance with certain embodiments of the present disclosure, a computer-based image processor may model an output of one or more equations relating a volume of the contrast agent within a given volume of enhanced contrast in an image with respective total signal responses from the given volume in at least two images produced at different energies. In certain embodiments, the at least two images may be monochromatic images produced from at least two polychromatic images by X-ray spectral imaging. By way of non-limiting example, such X-ray spectral imaging may be performed by a Gemstone Spectral Imaging system available from General Electric Company. In other embodiments, a single polychromatic source spectrum may be utilized to determine a composite linear or mass attenuation coefficient for a contrast agent based on the various strengths of the source spectrum at different energies. The composite attenuation coefficient may be related to an overall signal response of a given volume of a polychromatic image to determine an amount of the contrast agent in the image.

Figure 1:
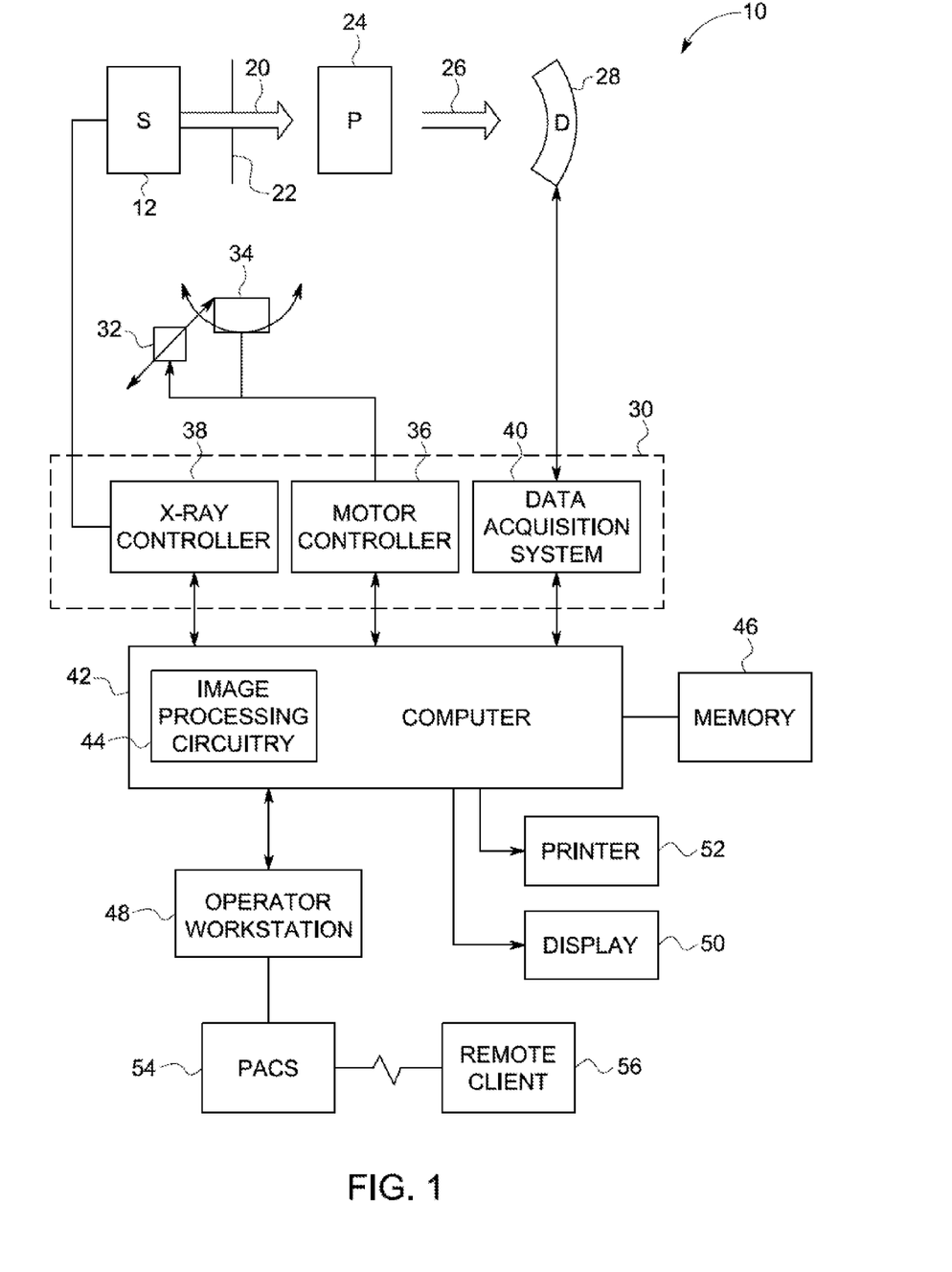
FIG. 1 is a schematic illustration of an embodiment of a computed tomography (CT) system configured to acquire CT images of a patient and process the images to determine an amount of a contrast agent within regions of the generated images.

FIG. 1 illustrates one such embodiment of an imaging system 10 for acquiring and processing image data to determine signal responses arising from a contrast agent. In the illustrated embodiment, system 10 is a computed tomography (CT) system designed to acquire X-ray projection data, to reconstruct the projection data into a tomographic image, and to process the image data for display and analysis. In the embodiment illustrated in FIG. 1, the CT imaging system 10 includes an X-ray source 12. As discussed in detail herein, the source 12 may include one or more X-ray sources, such as an X-ray tube. The X-ray source 12, in accordance with present embodiments is configured to emit an X-ray beam 20 at one or more energies. For example, the X-ray source 12 may be configured to switch between relatively low energy polychromatic emission (e.g., 40 kVp) and relatively high energy polychromatic emission (e.g., 140 kVp). Such variable emission may enable the system 10 to perform material density measurements using, by way of non-limiting example, spectral emission.

The source 12 may be positioned proximate to a collimator 22 used to define the size and shape of the one or more X-ray beams 20 that pass into a region in which a subject 24 (e.g., a patient) is positioned. The subject 24, which may include one or more contrast agent materials, attenuates at least a portion of the X-rays. Resulting attenuated X-rays 26 impact a detector array 28 formed by a plurality of detector elements. Each detector element produces an electrical signal that represents the intensity of the X-ray beam incident at the position of the detector element when the beam strikes the detector 28. Electrical signals are acquired and processed to generate one or more scan datasets.

A system controller 30 commands operation of the imaging system 10 to execute examination and/or calibration protocols and to process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12, and to process the data acquired by the detector 28. In one embodiment, the system controller 30 may be implemented as all or part of a processor-based system such as a general purpose or application-specific computer system.

The source 12 may be controlled by an X-ray controller 38 contained within the system controller 30. The X-ray controller 38 may be configured to provide power and timing signals to the source 12. In addition, in some embodiments the X-ray controller 38 may be configured to selectively activate the source 12 such that tubes or emitters at different locations within the system 10 may be operated in synchrony with one another or independent of one another.

The system controller 30 may include a data acquisition system (DAS) 40. The DAS 40 receives data collected by readout electronics of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer 42 may include or communicate with one or more non-transitory memory devices 46 that can store data processed by the computer 42, data to be processed by the computer 42, or instructions to be executed by a processor of the computer 42. For example, a processor of the computer 42 may execute one or more sets of instructions stored on the memory 46, which may be a memory of the computer 42, a memory of the processor, firmware, or a similar instantiation. In accordance with present embodiments, the memory 46 stores sets of instructions that, when executed by the processor, perform image processing methods. Embodiments of such methods are discussed in detail below with respect to FIGS. 3-7. As noted above, the memory 46 may also store instructions for converting two polychromatic measurements to material decomposition pairs (e.g., a water-iodine pair) and in turn generating monochromatic images, the process of which is referred to herein as spectral imaging (e.g., X-ray or CT spectral imaging). (e.g., a first monochromatic image at a first energy and a second monochromatic image at a second energy) from two or more polychromatic image acquisitions. Generally stated, such spectral imaging techniques enable the simulation of an image that would be produced from a truly monochromatic acquisition (i.e., imaging at a single energy).

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, contrast agent density maps produced in accordance with the present disclosure, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Figure 2:
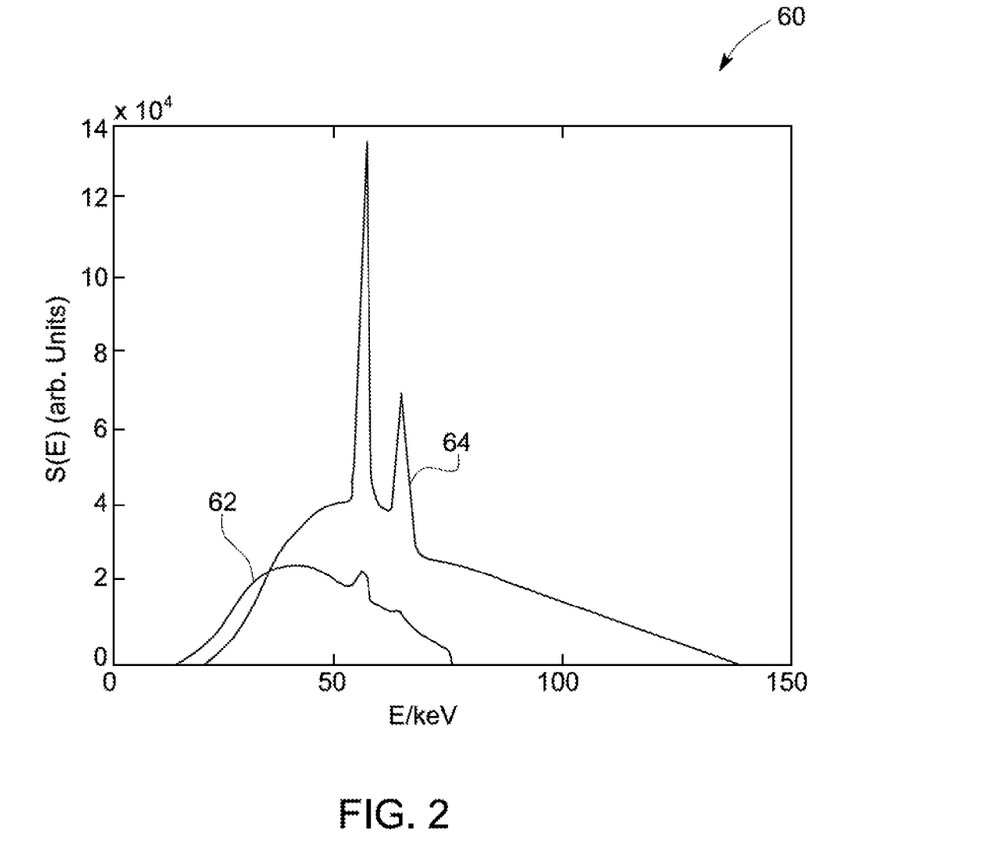
FIG. 2 is an embodiment of a plot of two different polychromatic source spectra generated by an X-ray source.

As noted above, the X-ray source 12 may be configured to emit X-rays at one or more energies. It should be noted, however, that the emission at a single energy for an X-ray source may constitute a polychromatic emission centered at, or having a peak strength at, the energy. A plot 60 illustrating an example of two source spectra emitted by the X-ray source 12 of FIG. 1 is depicted in FIG. 2. Specifically, the plot 60 of FIG. 2 provides a first source spectrum 62 and a second source spectrum 64. The plot 60 depicts the strength of the first and second source spectra 62, 64 on the Y-axis as a function of an emitted energy on the X-axis.

As depicted, the first source spectrum 62 represents an emission by the X-ray source 12 of approximately 80 kVp, or peak kilovolts, which represents the highest energy emitted in the first source spectrum 62. In accordance with present embodiments, this represents a first energy emitted by the X-ray source 12, and may also be referred to as a first polychromatic energy emission. The second source spectrum 64 represents an emission by the X-ray source of approximately 140 kVp. In one embodiment, the first source spectrum 62 may represent a lower energy emission and the second source spectrum 62 may represent a higher energy emission. As may be appreciated, these two source spectra may result in different images produced after X-ray imaging. Furthermore, the images so produced may be composite images containing attenuation information across the entire source spectra, rather than at a discreet single energy.

In accordance with present embodiments, it may be desirable to generate, using images produced from at least the first and second source spectra 62, 64, which may generally be any energy, simulated images that are true monochromatic images. As defined herein, a simulated monochromatic image is intended to denote an image that is produced by an image processing device to simulate, using at least two polychromatic images obtained using two different polychromatic source spectra, how an image would look, or what the data in an image would be, if the image were obtained using a true monochromatic source (i.e., a source that emits only one energy with no bandwidth). As discussed below with respect to FIGS. 3-6, the present embodiments provide approaches for modeling an amount of a contrast agent within a given volume of an image using the respective spectral responses of at least two monochromatic images produced from at least two polychromatic images.

Keeping in mind the operation of the system 10 and, specifically, the X-ray source 12 discussed above with respect to FIGS. 1 and 2, FIG. 3 illustrates a process flow diagram of an embodiment of a method 70 of image processing. Any suitable application-specific or general-purpose computer having a memory and processor may perform the method 70. By way of example, as noted above with respect to FIG. 1, the computer 42 and associated memory 46 may be configured to perform the method 70. For example, the memory 46, which may be any tangible, non-transitory, machine-readable medium (e.g., a disc, solid state device, chip, firmware), may store one or more sets of instructions that are executable by a processor of the computer 42 to perform the steps of method 70. In accordance with present embodiments, the processor, in performing method 70, may determine, estimate, or model an amount of contrast agent within a contrast-enhanced X-ray image, which may be a two-dimensional image or a three-dimensional volumetric image obtained using CT image acquisition and processing.

Figure 3:
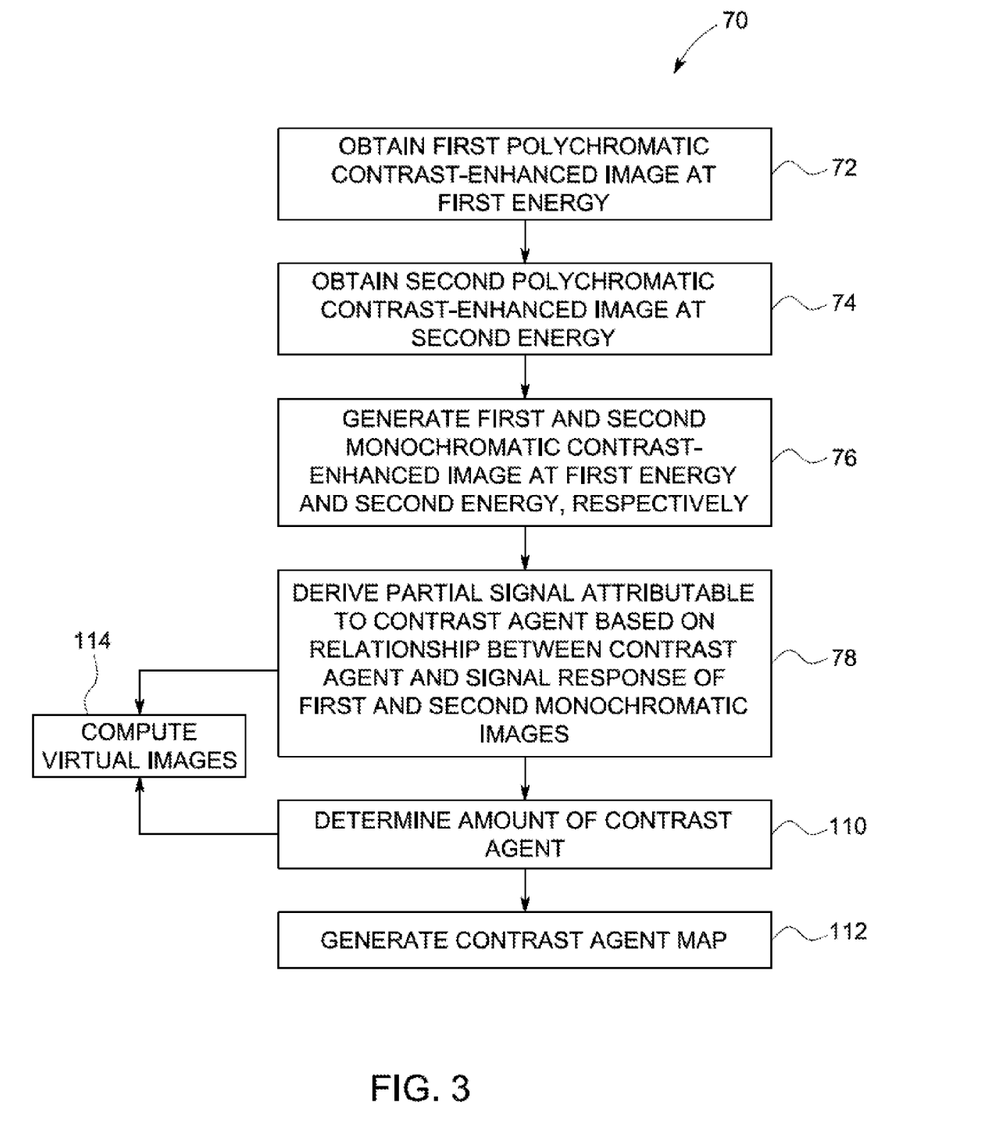
FIG. 3 is a process flow diagram illustrating an embodiment of a method for determining an amount of a contrast agent in an image using two or more monochromatic images simulated from two or more polychromatic images.

The method 70 includes obtaining a first polychromatic contrast-enhanced X-ray image at a first source energy (block 72), which is polychromatic. The acts associated with block 72 may be performed at the time of imaging the subject 24, or post-imaging. For example, obtaining the first polychromatic contrast-enhanced image may include performing imaging using the system 10 of FIG. 1 to generate the first image. Alternatively or additionally, the acts associated with block 72 may include accessing the first image from memory, such as from a local storage device or from an image archiving system, such as the PACS 54 of FIG. 1. Therefore, the acts associated with block 72 may be performed by the system 10, or by a computing device local to or remote from the facility in which the image is acquired. A second polychromatic contrast-enhanced X-ray image may then be obtained in a similar manner to the first image (block 74) at a second source energy, which is polychromatic.

Using the first and second polychromatic contrast-enhanced X-ray images obtained in accordance with blocks 72 and 74, first and second monochromatic contrast-enhanced X-ray images may be simulated (block 76). By way of non-limiting example, the first and second monochromatic images may be simulated using X-ray spectral imaging techniques. In accordance with certain embodiments, X-ray spectral imaging techniques may enable the measurement of a spectral response of an image at a single energy, rather than at a plurality of energies as is obtained using a polychromatic source. By way of example, as noted above, one such system that is configured to perform X-ray spectral imaging (e.g., spectral CT) is a Gemstone Spectral Imaging system available from General Electric Company. Thus, the first monochromatic image generated in accordance with block 76 may be simulated to contain data representative of a spectral response at a first single energy. It should be noted that the first single energy may or may not correspond to the peak energy of the source spectrum used to obtain the first polychromatic image (i.e., the peak energy of the first source energy). Similarly, the second monochromatic image generated in accordance with block 76 may be simulated to contain data representative of a spectral response at a second single energy. Again, the second single energy may or may not correspond to the peak energy of the second source energy used to obtain the second polychromatic image.

The attenuation of X-rays generally decreases with increasing energy of the X-rays incident on the attenuating material. Thus, at lower energies, it may be possible to image relatively low density materials, such as soft tissues, in addition to higher density materials. At higher energies, the lower density materials may not attenuate the X-rays to the same extent as the lower energies. Therefore, using the combination of high energy and low energy imaging may provide a more accurate depiction of the tissues and/or materials of interest in a given imaging routine. Indeed, the attenuation of materials may be more accurately measured using the monochromatic images generated in accordance with block 76. In accordance with present embodiments, as mentioned above, the signal responses of first and second monochromatic images may also be used to determine the relative amount of an attenuating material within a given volume of the images. Accordingly, the first and second monochromatic images are images of the same, or a similar volume.

Accordingly, in the method 70, once the first and second monochromatic images are generated/simulated, the partial signal attributable to a material of interest, such as a contrast agent, is able to be derived based on a relationship between the volume of contrast agent in a given volume of interest and the respective overall signal responses of the given volume in the first and second monochromatic images (block 78). It should be noted that the acts according to block 78 discussed below may be applicable in a number of different contexts for determining amounts, volumes, concentrations, or densities of attenuating materials. For example, the acts according to block 78 may be used for determining amounts of contrast agent present within a given volume of blood, for determining the density of calcium in a given volume of bone, and similar determinations. While the present approaches are applicable to any such context, the determination of contrast agent amounts within a given volume of blood will be discussed to facilitate the description of aspects of the present embodiments. For example, the approaches discussed herein may be applicable to CT angiography, CT venography, and/or CT perfusion studies. Furthermore, in some embodiments, the acts according to block 78 may include isolating regions of enhanced contrast from other regions of the images for further manipulation, and to facilitate computation, as discussed below.

As noted above, the volume of the contrast agent within a given imaged volume may be modeled based on a relationship between the volume of the contrast agent and the respective signal responses of the first and second monochromatic images. The overall signal response of a given volume v, such as a voxel for simplicity, at an energy E may be a function of, for CT perfusion studies, a combination of the linear attenuation coefficients of the blood within the voxel and the contrast agent within the voxel at the energy E. The voxel's linear attenuation coefficient at E, which determines the signal response of the voxel when imaged using energy E, is a combination of the mass attenuation coefficient of the voxel (volume v) $\mu_v(E)$ and the density of the voxel $\rho_v$. These parameters are defined using equations 1 and 2 below:

$$\mu_v(E) = \frac{(x\rho_c\mu_c(E) + (v-x)\rho_b\mu_b(E))}{(x\rho_c + (v-x)\rho_b)} \quad (1)$$

$$\rho_v = \frac{(x\rho_c + (v-x)\rho_b)}{v} \quad (2)$$

where x is the volume occupied by the contrast agent within the volume v, $\rho_c$ is the known density of the contrast agent, $\mu_c(E)$ is the known mass attenuation coefficient of the contrast agent at the energy E, (v−x) is the volume of blood within the volume v, $\rho_b$ is an assumed density of the blood, and $\mu_b(E)$ is the known mass attenuation coefficient of the blood (e.g., based on an assumed composition) at the energy E. In certain embodiments, the mass attenuation coefficients of certain contrast agents are known for various energies. However, in embodiments where these values are not known, the mass attenuation coefficients may be determined using equation 3:

$$\mu_c = \sum_{i=1}^{n} \frac{m_i}{M} * \mu_i \quad (3)$$

where $m_i$ is the mass of a given atom of the contrast agent compound, $\mu_i$ is the mass attenuation coefficient of the atom at a particular energy, and M is defined by:

$$M = \sum_{i=1}^{n} m_i. \quad (3a)$$

Mass attenuation constants for various atoms (i.e., $\mu_i$) at various energies may be obtained from National Institute of Standards and Technology (NIST) values. Linear attenuation coefficients may be obtained from the mass attenuation coefficients via multiplication by the known/measured density of the material (i.e., the known/measured density of the contrast agent). A table listing example organic iodine-based contrast agents and their associated properties is provided in Table 1 below.

TABLE 1

Properties of Various Contrast Agents

| Trade Name | Contrast Agent | Contrast Agent (mg/mL) | Iodine (mg/mL) | Density |
|---|---|---|---|---|
| OMNIPAQUE ® | iohexol | 518 | 240 | 1.28 |
| | | 647 | 300 | 1.349 |
| | | 755 | 350 | 1.406 |
| VISIPAQUE ® | iodixanol | 550 | 270 | 1.303 |
| | | 652 | 320 | 1.356 |
| ISOVUE ® | iopamidol | 408 | 200 | 1.227 |
| | | 510 | 250 | 1.281 |
| | | 612 | 300 | 1.339 |
| | | 755 | 370 | 1.405 |

OMNIPAQUE® radiographic contrast agent is commercially available as an injectible solution from General Electric Healthcare. OMNIPAQUE® radiographic contrast agent uses iohexyl (C-1) (N,N'-bis(2,3-dihydroxypropyl)-5-[N-(2,3-dihydroxypropyl)-acetamido]-2,4,6-triiodoisophthalamide), which has the chemical structure:

C-1

VISIPAQUE® radiographic contrast agent is also commercially available as an injectible solution from General Electric Healthcare. VISIPAQUE® radiographic contrast agent uses iodixanol (C-2) (5,5'-[(2-hydroxy-1,3-propanediyl)bis(acetylimino)]bis[N,N'-bis(2,3-dihydroxypropyl)-2,4,6-triiodo-1,3-benzenedicarboxamide), which has the following chemical structure:

C-2

ISOVUE® radiographic contrast agent is commercially available as an injectible solution from Bracco Diagnostic, Inc. ISOVUE® radiographic contrast agent utilizes iopamidol (C-3) ((S)—N,N'-bis[2-hydroxy-1-(hydroxymethyl)-ethyl]-2,4,6-triiodo-5-lactamidoisophthalamide). Iopamidol has the following chemical structure:

C-3

As noted above, the overall structure of the contrast agents, including relatively highly attenuating atoms such as iodine and relatively low attenuating atoms such as carbon and hydrogen, contribute to the contrast enhancement provided by the contrast agent, which is a function of the mass attenuation coefficient of the contrast agent molecule. Accordingly, it may be appreciated that each contrast agent may have a different mass attenuation coefficient resulting from these differences in molecular structure, and, accordingly, may provide different contrast enhancement. More particularly, the linear attenuation coefficient of the contrast agent, which is a product of the mass attenuation coefficient and the density of the contrast agent, may provide the signal response attributable to the contrast agent.

Figure 4:
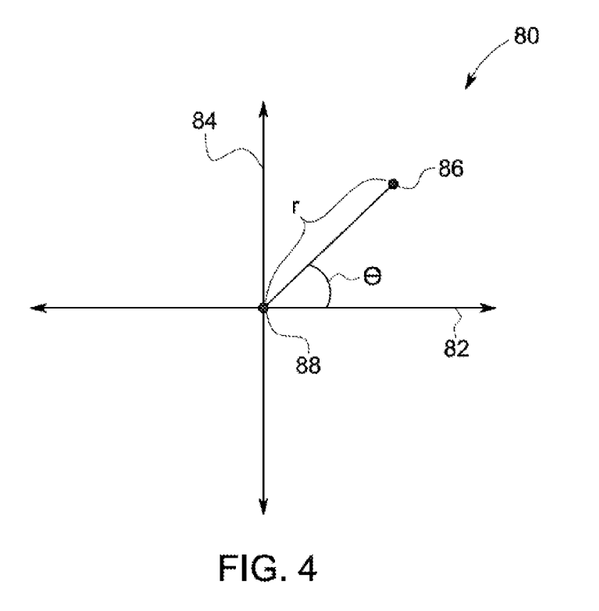
FIG. 4 is an embodiment of a Cartesian plot representing a signal response of a volume at two different energies, the plot having an origin at the signal response of water at the two energies.

The linear attenuation coefficient of the volume v, which, as noted above, is dependent on the respective amounts and linear attenuation coefficients of blood and contrast agent in the volume v, is considered to be in the attenuation space. The linear attenuation coefficient of the volume v is directly related to the signal response of the volume v, which may be considered a region of enhanced contrast and may be measured in Hounsfield Units (HU), in the image space. In accordance with present embodiments, the overall signal responses at two distinct energies in the image space of the volume v, which may, in certain embodiments, be separated from non-enhanced regions at two energies to generate a first region of enhanced contrast and a second region of enhanced contrast, may be represented as a set of Cartesian coordinates. In some embodiments, the set of Cartesian coordinates (i.e., the signal responses) may be plotted to relate the image space signal response at the two energies to an amount of the contrast agent. One such plot 80 is illustrated in FIG. 4. In the plot 80, axis 82 is the $HU_{E1}$ value (i.e., a value of the first region of enhanced contrast at the first single energy) and axis 84 is the $HU_{E2}$ value (i.e., a value of the second region of enhanced contrast at the second single energy). Accordingly, point 86 is defined by the signal response of the volume v at a first energy, $HU_{E1}$, and the signal response of the volume v at a second energy $HU_{E2}$, where $HU_{E1}$ is the X-coordinate and $HU_{E2}$ is the Y-coordinate. This Cartesian coordinate point 86 represents a combined signal response for the volume v at the first and second single energies.

Similarly, an origin point 88 of the plot 80 represents the combined signal response at the first and second single energies of water. Therefore, point 86 graphically depicts the signal response of the volume v in relation to water at the origin point 88. As illustrated, the relative positioning of point 86 and point 88 may be represented by a distance r between their respective positions in the plot 80. Furthermore, r may also be related to the axis 82, which represents $HU_{E1}$, by $\theta$. $\theta$, as illustrated, is the angle between a line created by distance r and the axis 82. In one embodiment, the signal response of the volume v at the first and second single energies may be represented by r and $\theta$, which are defined by equations 4 and 5 below.

$$r(E1, E2) = \sqrt{HU_{E2}^2 + HU_{E1}^2} \qquad (4)$$

$$\theta(E1, E2) = \tan^{-1}\frac{HU_{E2}}{HU_{E1}} \qquad (5)$$

In accordance with present embodiments, the distance r between point 86 and origin point 88 is correlated to the volume x of contrast agent present within the given volume v. In addition, as set forth above, the volume x of contrast agent is related to the attenuation of the overall volume. Therefore, the signal response in the image space (i.e., HU value) may be converted to the attenuation space by equation 6 below.

$$HU = \frac{\mu_{material}\rho_{material} - \mu_{water}\rho_{water}}{\mu_{water}\rho_{water} - \mu_{air}\rho_{air}} * 1000 \qquad (6)$$

In accordance with certain embodiments, $\mu_{material}\rho_{material}$ is the combined signal response of the blood and the contrast agent within the volume v. Accordingly, using the equations above and performing the appropriate substitutions, x and r may be related by a first equation, and x and $\theta$ may be related by a second equation. Specifically, in accordance with present embodiments, x and r may be related by equation 7 below:

$$r^2 = Ax^2 + Bx + C \qquad (7)$$

and A, B, and C are defined as:

$$A = \frac{(\mu_c(E_2)\rho_c - (\mu_b(E_2)\rho_b)^2}{(\mu_w(E_2)\rho_w)^2 v^2} + \frac{(\mu_c(E_1)\rho_c - (\mu_b(E_1)\rho_b)^2}{(\mu_w(E_1)\rho_w)^2 v^2} \qquad (7a)$$

$$B = \frac{2\mu_c(E_2)\rho_c\mu_b(E_2)\rho_b v - 2(\mu_b(E_2)\rho_b)^2 v -}{(\mu_w(E_2)\rho_w)^2 v^2} + \frac{2(\mu_w(E_2)\rho_w)v(\mu_c(E_2)\rho_c - \mu_b(E_2)\rho_b)}{(\mu_w(E_2)\rho_w)^2 v^2} +$$

$$\frac{2\mu_c(E_1)\rho_c\mu_b(E_1)\rho_b v - 2(\mu_b(E_1)\rho_b)^2 v -}{2(\mu_w(E_1)\rho_w)v(\mu_c(E_1)\rho_c - \mu_b(E_1)\rho_b)}$$
$$\overline{(\mu_w(E_1)\rho_w)^2 v^2}$$

$$C = \frac{(\mu_b(E_2)\rho_b - (\mu_w(E_2)\rho_w)^2}{(\mu_w(E_2)\rho_w)^2} + \frac{(\mu_b(E_1)\rho_b - (\mu_w(E_1)\rho_w)^2}{(\mu_w(E_1)\rho_w)^2}. \qquad (7c)$$

Figure 5:
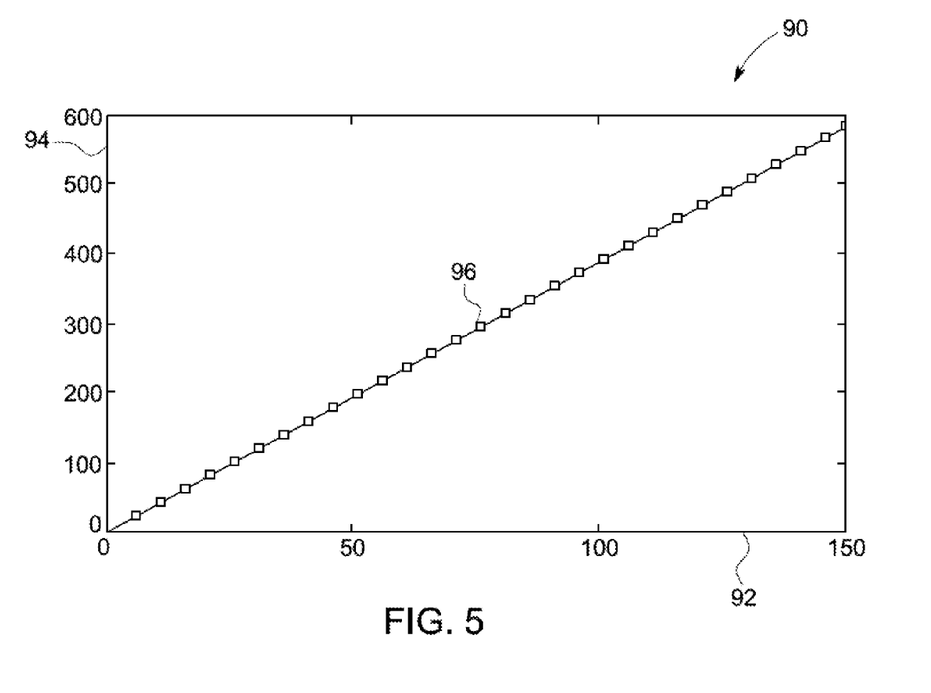
FIG. 5 is an embodiment of a plot of contrast agent volume as a function of the signal responses plotted in FIG. 4.

Using the relationship set forth in equation 7, a known contrast agent molecular configuration, and the known mass attenuation coefficient/linear attenuation coefficient for the contrast agent, a series of outputs of equation 7 may be plotted to model the dependence of x on r for a given contrast agent. An embodiment of one such plot 90 is illustrated in FIG. 5. Specifically, in FIG. 5, in which axis 92 represents r and axis 94 represents x, x may be plotted as a function of r to generate line 96. The line 96 may be used to determine x for a given r. Accordingly, by way of example, plot 90 may be representative of the relationship between the volume of one particular contrast agent and the signal response of two monochromatic images having a partial signal attributable to the particular contrast agent. It should therefore be noted that one such plot may be generated for each contrast agent used in a particular study. Further, using plots such as plot 90 may enable the generation of one or more look up tables setting forth various contrast agent volumes depending upon signal responses in monochromatic images.

As noted above, $\theta$ may, as an alternative to r or in addition to r, be used to model x. Thus, in accordance with an embodiment, x and $\theta$ are related by equation 8 below:

$$S = Px + Qx\tan\theta + R\tan\theta \qquad (8)$$

and P, Q, R, and S are defined as:

$$P = -(\mu_c(E_2)\rho_c - \mu_b(E_2)\rho_b)\phi_w \qquad (8a)$$

$$Q = \mu_c(E_2)\rho_c - \mu_b(E_2)\rho_b \qquad (8b)$$

$$R = (\mu_b(E_1)\rho_b - \mu_w(E_1)\rho_w)v \qquad (8c)$$

$$S = (\mu_b(E_2)\rho_b - \mu w(E_2)\rho_w)v\phi_w. \qquad (8d)$$

Figure 6:
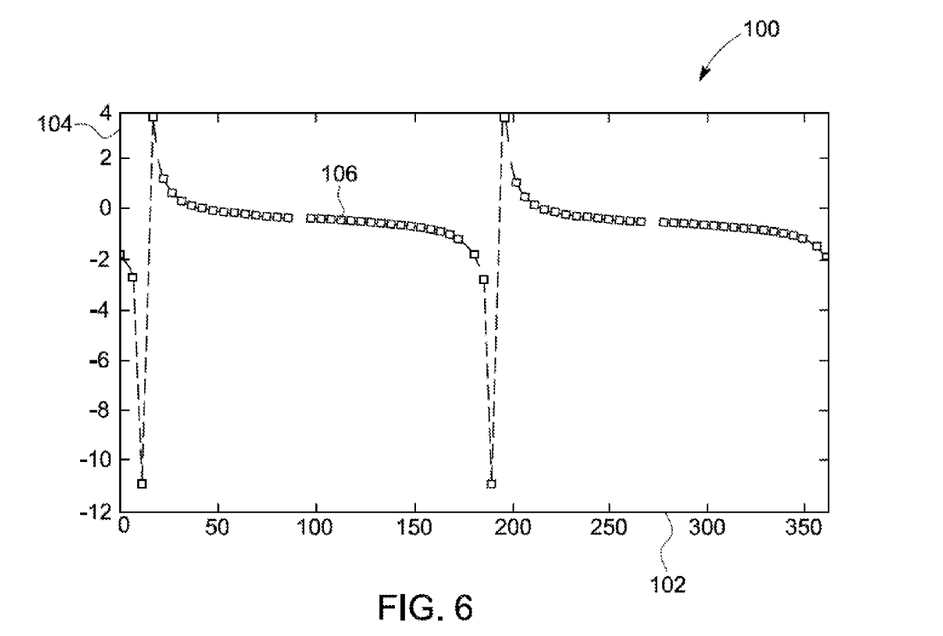
FIG. 6 is an embodiment of a plot of contrast agent volume as a function of the signal responses plotted in FIG. 4.

Using the trigonometric relationship set forth in equation 8, a known contrast agent molecular configuration, and the known mass attenuation coefficient/linear attenuation coefficient for the contrast agent, a series of outputs of equation 8 may be plotted to model the dependence of x on $\theta$ for a given contrast agent. An embodiment of one such plot 100 is illustrated in FIG. 6. Specifically, in FIG. 6, in which axis 102 represents $\theta$ and axis 104 represents x, x may be plotted as a function of $\theta$ to generate trigonometric line 106.

While the line 106 may be used to determine x for a given $\theta$ as in FIG. 5, it will be appreciated that, for certain values of $\theta$, x may not be defined in FIG. 6. For example, in the plot 100, certain values of $\theta$ result in negative values for x, which is a result of the trigonometric relationship between $\theta$ and x. As noted above with respect to FIG. 5, a plot similar to plot 100 may be generated for each contrast agent used in a particular study. Further, using plots such as plot 100 may enable the generation of one or more look up tables setting forth various contrast agent volumes depending upon signal responses in monochromatic images. Indeed, in certain embodiments, both plots 90 (FIG. 5) and 100 may be used to estimate a volume of contrast agent within a given imaged volume. Therefore, plot 90 of FIG. 5, plot 100 of FIG. 6, or a combination thereof, may be used to determine the volume x of the contrast agent in the given imaged volume, which may be a contrast-enhanced voxel, vessel, or any volume that is able to be separated from other non-contrast-enhanced regions of the images.

Returning to the method 70 of FIG. 3, the estimated/determined volume x of the contrast agent (i.e., the partial signal attributable to the contrast agent) within the given volume (e.g., voxel) may be used to determine the actual amount of the contrast agent (block 110). For example, the volume x obtained via method 70 may be multiplied by the known density of the contrast agent to determine an amount of the contrast agent within the volume v. Therefore, alternatively or additionally, it may be desirable to identify an overall density of the contrast agent within the volume v. Accordingly, the amount of the contrast agent may be divided by the volume v to determine the density of the contrast agent within the given volume.

As discussed below, the determined amount and/or density may be used to generate a contrast agent map of over the regions of enhanced contrast. In certain embodiments, it may be desirable to also determine the amount of an attenuating atom (e.g., iodine) of the contrast agent, which may enable direct comparisons between scans and/or between contrast agents. Accordingly, in such embodiments, based on the determined volume x of the contrast agent, the amount of the contrast agent (e.g., in grams), the volume fraction of the agent (e.g., x/v), or any combination thereof, the amount of the attenuating atom (e.g., a volume and/or amount) of the attenuating atom may be determined. Furthermore, the density of the attenuating atom may be determined using the volume v of the given volume (e.g., the voxel). Thus, the amount of the contrast agent and/or the attenuating atom (e.g., iodine) may be represented as an amount (e.g., grams), a volume fraction, a density (e.g., mass iodine/v, mass contrast agent/v).

A table of example cases, along with a computed iodine dose and iodine density for each case, is provided below. In the example cases, contrast enhanced CT exams were taken using a GSI HDCT scanner available from General Electric Healthcare using OMNIPAQUE 300® contrast agent. The basilar artery region was chosen for the injection of the contrast agent solution in head cases, while the left common carotid was chosen in head-neck cases. Given the volume of the section of vessel in cubic centimeters (cc), and the mean signal response intensity in HU, the computed "score" captured the percentage of the contrast agent solution in the given volume of the blood. Using the information from the contrast agent and its composition used for the scan, the iodine dose was computed in milligrams of iodine (mgI), and the iodine density in mg/mL was subsequently computed. The estimated contrast agent doses across the multiple cases are reported in Table 2 below.

TABLE 2

Estimated Iodine Dose and Density Across Various Cases

| Case No. | Volume (cc) | Mean HU | Score | Iodine dose (mgI) | Iodine density (mg/mL) |
|---|---|---|---|---|---|
| 1 | 3.89 | 158 | 1.326 | 15.51 | 3.98 |
| 2 | 0.76 | 169 | 1.467 | 3.35 | 4.40 |
| 3 | 2.92 | 225 | 2.185 | 19.19 | 6.57 |
| 4 | 1.88 | 240 | 2.377 | 13.44 | 7.14 |
| 5 | 2.45 | 248 | 2.479 | 18.27 | 7.45 |
| 6 | 0.79 | 260 | 2.633 | 6.27 | 7.93 |
| 7 | 3.76 | 299 | 3.133 | 35.44 | 9.42 |
| 8 | 3.99 | 332 | 3.556 | 42.64 | 10.68 |
| 9 | 2.59 | 404 | 4.478 | 34.94 | 13.49 |
| 10 | 2.04 | 489 | 5.567 | 34.17 | 16.75 |

Using the determined amount of contrast agent, the determined density of contrast agent, the determined amount of attenuating atom of interest, or the determined density of the attenuating atom of interest, a map may be generated (block 112). For example, a map of the relative level of contrast agent and/or attenuating atom of interest may be overlaid on any of the images mentioned above, or may be generated as a standalone image/map. In such maps, regions of relatively high contrast may represent the relative level of contrast agent/attenuating atom of interest within a given area. For example, brighter areas may represent higher levels of contrast agent/attenuating atom of interest. Additionally, such mapping may enable one or more analyses of perfusion. For example, the contrast agent may perfuse from the vasculature to the extravascular space, which enables the analysis of, by way of example, perfusion volume and perfusion kinetics.

As illustrated, the method 70 may include, in addition to or as an alternative to generating the contrast agent map in accordance with block 112, computing one or more virtual images (block 114) using the partial signal attributable to the contrast agent obtained in accordance with block 78, or using the density of iodine in a given image volume obtained in accordance with block 110, or a combination thereof. For example, the one or more virtual images may include contrast-normalized images, virtual high contrast images, and virtual images where an original contrast agent is virtually substituted with another contrast agent.

To produce contrast-normalized images, areas having relatively large amounts of contrast agent (evidenced by a higher relative contrast) and/or areas having relatively low amounts of contrast agent (evidenced by a lower relative contrast) may be adjusted. Such approaches may be desirable in situations where a given contrast agent has "pooled" within a tissue region. Pooling can result in very high levels of contrast within a small volume, which may hinder vascular analyses in regions proximate the area where the contrast agent has pooled. Accordingly, normalizing/adjusting contrast can, in certain situations, facilitate analyses of contrast-enhanced images.

In an embodiment, a virtual image may be produced by virtually enhancing the contrast of regions in a given imaged volume that have relatively low contrast to levels that are substantially similar to the contrast of those regions having higher contrast agent amounts (and, therefore, higher contrast). Indeed, in certain embodiments, the virtual image may be produced by computing a substantially constant iodine density image from the original image, which enables the visualization of vessels that may not be perfused with adequate amounts of contrast agent. By way of example, a normalized virtual image may be produced by virtually adjusting an amount of contrast agent (e.g., the iodine dose) to a substantially constant level across the vessels in a given imaged volume.

In another embodiment, a virtual image may be produced by computationally adjusting a maximum level of contrast within the imaged volume. For example, upon calculating the amount of contrast agent across the imaged volume, a thresholding function may be applied that limits a maximum level of contrast to a certain dose of the contrast agent. In one embodiment, this may be accomplished by limiting a maximum dose of contrast agent or dose of attenuating element (e.g., iodine) to a particular level across the imaged volume. Thus, a virtual image may be produced from an obtained contrast-enhanced image by computationally reducing (e.g., clipping) the contrast agent dose in areas having a contrast agent dose above a chosen threshold.

In addition to, or in lieu of, producing virtual images by adjusting an amount of a given contrast agent in a given imaged volume, it may be desirable to virtually replace one contrast agent for another. That is, in one embodiment in accordance with the present disclosure, a virtual image may be produced from an obtained contrast-enhanced image by virtually replacing a first contrast agent in the obtained image with a second contrast agent to produce the virtual image. This replacement may be accomplished by computing conversion factors between contrast agents (e.g., via their respective signal responses), and adjusting the level of contrast in the obtained image to new contrast levels based on the conversion factor from the first contrast agent to the second contrast agent. For example, Table 3 below provides an example of the manner by which two different contrast agents, OMNIPAQUE® radiographic contrast agent and ISOVUE® radiographic contrast agent, may have varying responses over different imaging energies. In particular, the differential response signal due to the difference in molecular structure across the two contrast agents is provided. In Table 3, the agents are normalized to the same equivalent density of Iodine (300 mg/mL). In addition, the response of each agent at different concentrations and at different energies in a mixture with blood is computed. Given that the iodine density is constant, the difference of signal can be attributed to the difference in the molecular composition of each agent. Accordingly, it may be appreciated that a look-up table, conversion chart, or the like, may be produced from similar data to enable the replacement of one contrast agent for another.

TABLE 3

Effect of Molecular Structure on Iodine Contrast Agent Signal Response

| Energy (keV) | Contrast Agent Volume Fraction | OMNIPAQUE ® (HU) | ISOVUE ® (HU) | Difference |
|---|---|---|---|---|
| 40 | 0.004 | 170.75 | 170.67 | 0.008 |
|  | 0.04 | 1060 | 1059.3 | 0.7 |
|  | 0.4 | 9952.5 | 9945.1 | 7.4 |
| 140 | 0.004 | 59.48 | 59.46 | 0.02 |
|  | 0.04 | 116.27 | 116.07 | 0.2 |
|  | 0.4 | 684.15 | 682.21 | 1.94 |
| 70 | 0.004 | 85.79 | 85.64 | 0.15 |
|  | 0.04 | 366.75 | 365.29 | 1.46 |
|  | 0.4 | 3176.4 | 3161.8 | 14.6 |

While Table 3 above illustrates the manner by which two iodine-based radiographic contrast agents may be interconverted, it should be noted that the expected response of other agents, such as agents typically used for magnetic resonance imaging (MRI), may be computed. Therefore, the expected X-ray imaging signal response of an agent typically used for MRI (e.g., a gadolinium-based agent) may be used to virtually replace the signal response of an iodine-based agent. For example, the expected signal response of a given material (e.g., the gadolinium-based agent) at a given energy may be computed using the mass attenuation coefficient of the agent at that energy, which may be obtained based on the molecular structure of the agent as set forth above.

Table 4 below provides the expected response of two gadolinium contrast agents primarily used in MRI. In particular, OMNISCAN® MRI contrast agent, available as an injectible solution from General Electric Healthcare, uses gadodimide (C-4) (gadolinium(III) 5,8-bis(carboxylatomethyl)-2-[2-(methylamino)-2-oxoethyl]-10-oxo-2,5,8,11-tetraazadodecane-1-carboxylate hydrate) to provide contrast, and is provided as one example. Gadodimide has the chemical structure:

C-4

In addition, VASOVIST™ MRI contrast agent, available as an injectible solution from Bayer Healthcare, Inc., uses gadofosveset trisodium (C-5) (trisodium-{(2-(R)-[(4,4-diphenyl-cyclohexyl)phosphonooxymethyl]-diethylenetriaminepentaacetato)(aquo) gadolinium(III)) to provide contrast, and is provided as another example in Table 4 for comparison. Gadofosveset trisodium has the chemical structure:

C-5

For the computations used to produce Table 4, the same volume of the agents is assumed to have been injected into the patient's bloodstream. The difference in the response is therefore due to variable response of the molecular structure of the agents. In particular, the difference in the response is attributable to the difference in organic carrier agent used to chelate the gadolinium ion. 50.24 keV was utilized for these results because it is the k-edge for Gadolinium.

TABLE 4

Effect of Molecular Structure on Gadolinium Contrast Agent Signal Response

| Energy (keV) | Contrast Agent Volume Fraction | OMNISCAN ® (HU) | VASOVIST ™ (HU) | Difference |
|---|---|---|---|---|
| 50.24 | 0.004 | 89.77 | 77.7 | 12.07 |
|  | 0.04 | 315.04 | 194.42 | 120.62 |
|  | 0.4 | 2567.8 | 1361.6 | 1206.2 |
| 140 | 0.004 | 55.8 | 54.5 | 1.3 |
|  | 0.04 | 79.5 | 67.2 | 12.3 |
|  | 0.4 | 316.2 | 193.6 | 122.6 |
| 70 | 0.004 | 67.1 | 61.1 | 6 |
|  | 0.04 | 179.6 | 119.6 | 60 |
|  | 0.4 | 1304.7 | 405.16 | 599.54 |

Using the expected signal response from the agents listed in Table 4 above, the response of the gadolinium agent may be used in place of the actual response obtained in for an iodine-based agent to generate a virtual image. Indeed, in accordance with the present approaches, the mass attenuation coefficient and, therefore, the expected signal response, may be calculated for any molecular configuration to generate a virtual image from a contrast-enhanced image obtained in accordance with present embodiments.

Further, it should be noted that in certain embodiments, a technician or similar healthcare person may obtain a set of monochromatic images that have been simulated at another location or facility. For example, the polychromatic images may be acquired, and the monochromatic images may be simulated at one or more separate facilities, and then provided to the technician. Accordingly, a system used by the technician may perform all of the steps of method 70, or only some of the steps (e.g., blocks 78, 110, 112, or any combination thereof).

While the approaches described above may be applicable to situations where simulated monochromatic images may be obtained, in some embodiments, it may be desirable to determine contrast agent amounts without the use of X-ray spectral imaging (e.g., spectral CT imaging), such as in situations where a system may not be suitably configured to perform spectral imaging. Accordingly, the present embodiments also provide a method 120, illustrated as a process flow diagram in FIG. 7, for the determination of a contrast agent volume based on a relationship between a composite mass attenuation coefficient for a contrast agent and the overall signal response of an isolated region of enhanced contrast, i.e., volume v.

Figure 7:
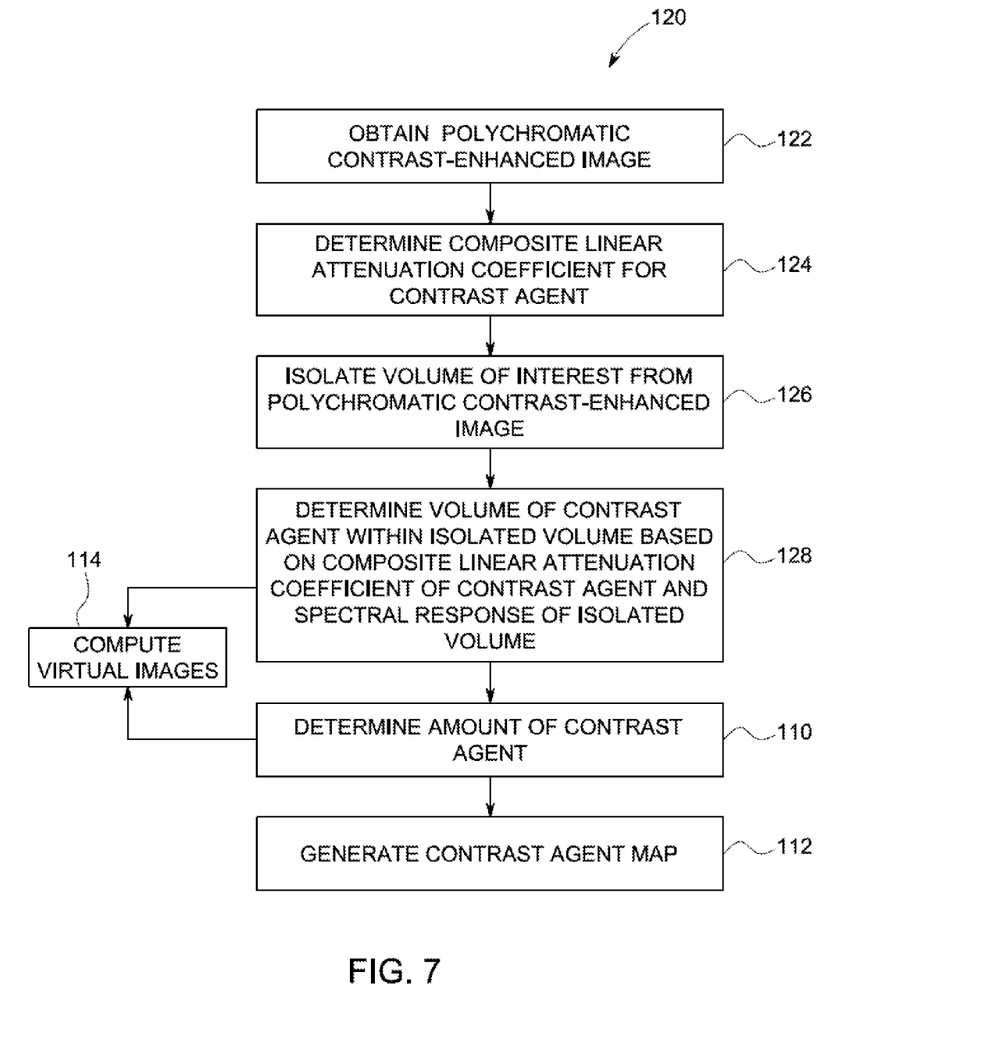
FIG. 7 is a process flow diagram illustrating an embodiment of a method for determining an amount of a contrast agent in an image using composite linear attenuation coefficients determined for a given polychromatic source spectrum used to generate a polychromatic X-ray image.

As with method 70, any suitable application-specific or general-purpose computer having a memory and processor may perform the method 120. By way of example, as noted above with respect to FIG. 1, the computer 42 and associated memory 46 may be configured to perform the method 120. For example, the memory 46, which may be any tangible, non-transitory, machine-readable medium (e.g., a disc, solid state device, chip, firmware), may store one or more sets of instructions that are executable by a processor of the computer 42 to perform the steps of method 120. In accordance with present embodiments, the processor, in performing method 120, may determine, estimate, or model an amount of contrast agent within a contrast-enhanced X-ray image, which may be a two-dimensional image or a three-dimensional volumetric image obtained using CT image acquisition and processing.

The method 120 includes obtaining a polychromatic contrast-enhanced image (block 122). The source spectra 62, 64 illustrated in FIG. 2 are each examples of polychromatic source spectra, which may each used to generate respective polychromatic contrast-enhanced images. As set forth above with respect to FIG. 1, the X-ray source 12 may generate such a polychromatic source spectrum having a peak kilovoltage (kVp). Accordingly, by way of example and as noted above, an imaging routine performed at 80 kVp may result in the X-ray source 12 emitting the source spectrum 62 of FIG. 2. It should be noted that each X-ray source may produce different source spectra at different imaging energies. In other words, a first X-ray source may produce a first polychromatic source spectrum at 80 kVp, and a second X-ray source may produce a second polychromatic source spectrum at 80 kVp. The first and second polychromatic source spectra may differ in their respective strengths at particular energies. For example, the first polychromatic source spectrum may have a lower strength of emission at 40 keV than the second polychromatic source spectrum.

Before or after obtaining the polychromatic contrast-enhanced image in accordance with block 122, a composite linear attenuation coefficient is determined for the contrast agent (block 124). In accordance with present embodiments, the composite mass attenuation coefficient may be generated by a weighted sum of linear attenuation coefficients for the contrast agent across a range of energies E1 to E2 emitted by the X-ray source 12 (FIG. 1), which may each be known or directly calculated as described above.

The composite linear attenuation coefficient for the contrast agent, $k^p$, may be determined by equation 9, which is a weighted sum of the linear attenuation coefficients of the contrast agent, k(i), over the range of energies emitted by the X-ray source 12.

$$k^p = \sum_{i=E1}^{E2} \alpha(i)k(i) \qquad (9)$$

The weight given to each attenuation coefficient is determined by the strength of the source spectrum at that particular energy, $\alpha(i)$. Similar operations may also be performed for blood to obtain a composite linear attenuation coefficient for blood, $k_b^p$. Specifically, $k_b^p$ is generated using assumed attenuation coefficients at varying energies, which may also be based on NIST values.

The method 120 may, in some embodiments, also include isolating a region of enhanced contrast from other portions of the polychromatic image (block 126). Such isolation may be performed in the image space or the attenuation space. In other embodiments, such regions may not be isolated. In certain embodiments, it may be desirable to isolate such regions to simplify certain processor-intense calculations associated with the method 120. In certain embodiments, the volume v may be isolated from other regions of the image.

Based on the composite linear attenuation coefficients of the contrast agent and blood and the overall signal response of the volume v from the polychromatic image, the volume x of the contrast agent within the volume v is determined (block 128). In accordance with present embodiments, equations 1 and 2 may be combined, and x may be isolated to determine the volume of the contrast agent according to equation 10:

$$x = v \frac{k_v^p(E) - k_b^p(E)}{k_c^p(E) - k_b^p(E)} \qquad (10)$$

where $k_b^p(E)$ is the composite linear attenuation coefficient for blood determined for the polychromatic source spectrum generated by the X-ray source at energy E, $k_c^p(E)$ is the composite linear attenuation coefficient for the contrast agent determined for the polychromatic source spectrum generated by the X-ray source at energy E, and $k_v^p(E)$ is the composite linear attenuation coefficient for the volume v at the energy E. In accordance with present embodiments, $k_v^p(E)$ may be related to the overall signal response of the volume v to determine x.

As noted above with respect to equation 5, the volume v (e.g., a voxel) may be a mixture of contrast agent and blood. In equation 5, the linear attenuation coefficient of this mixture is represented by $\mu_{material}\rho_{material}$. Solving for this term in equation 5, and assuming that $\mu_{material}\rho_{material}$ is the linear attenuation coefficient of the volume v, equation 11 is obtained, which relates the observed signal response in HU to the composite linear attenuation coefficient of the volume v:

$$k_v^p(E) = (k_{water}^p(E) - k_{air}^p(E))\frac{I_{HU}}{1000} + k_{water}^p(E) \qquad (11)$$

where $k_{water}^p(E)$ and $k_{air}^p(E)$ are the composite linear attenuation coefficients for water and air, respectively, determined for the polychromatic source spectrum generated by the X-ray source at energy E. $I_{HU}$ represents, in Hounsfield units, the overall signal response of the volume v in the polychromatic image. Accordingly, given a polychromatic source spectrum generated by an X-ray source at the energy used for imaging, the chemical structure of a contrast agent, and the overall signal response of the volume v, the acts according to block 128 enable the determination of the volume of the contrast agent, x.

Upon determining the volume x, it may be desirable, as noted above with respect to FIG. 3, to generate a map representing the amount of the contrast agent in a given imaged region. Thus, the amount of contrast agent and/or attenuating atom of interest may be determined in accordance with block 110 discussed above with respect to FIG. 3. Further, in certain embodiments, a map of the contrast agent and/or the attenuating atom of interest may be generated in accordance with block 112, which is discussed above with respect to FIG. 3.

In addition or in lieu of generating a map of the contrast agent or attenuating atom in accordance with block 112, as set forth above, one or more virtual images may be computed using the obtained volume x of the contrast agent and/or using the amount of contrast agent and/or attenuating atom of interest obtained in accordance with block 112 (block 114). Therefore, the one or more virtual images may include contrast-normalized images, virtual high contrast images, and virtual images where an original contrast agent is virtually substituted with another contrast agent, as discussed above with respect to FIG. 3.

Using any one or a combination of the approaches described above, the present disclosure also enables the comparison of signal responses across multiple contrast agents to ultimately obtain a target contrast enhancement using a known protocol for a single agent. For example, as discussed above and as set forth in Table 5 below, different contrast agents may deposit varying concentrations of iodine in the patient's bloodstream after injection. Table 5 depicts that for a constant target enhancement (HU(E)), different iodine doses would be given to the patient for different contrast agents.

TABLE 5

Constant Targeted Signal Response for Different Contrast Agents

| Contrast Agent | Contrast Agent Volume Fraction | Iodine Density (mg/mL) | Total Iodine per 5 liters blood (g) |
| --- | --- | --- | --- |
| OMNIPAQUE ® 300 | 0.0827 | 24.7667 | 123.8 |
| VISIPAQUE ® 270 | 0.0923 | 24.9377 | 124.7 |
| ISOVUE ® 370 | 0.0673 | 24.9155 | 124.6 |

Table 6 demonstrates the manner in which equivalent contrast dose may be obtained across different agents to achieve a target HU enhancement at an energy (E). The listed computation accounts for the differential signal across agents (i.e., the molecular structure differences between the agents). As an example, if X ml of OMNIPAQUE® 300 radiographic contrast agent was used to reach a 700HU enhancement at 70 keV, 81% of X ml of ISOVUE® 370 radiographic contrast agent would be used to achieve substantially the same enhancement. Such conversions could be utilized to achieve similar image contrast quality using any contrast agent with reference to a known clinical protocol for a single agent.

TABLE 6

Equivalent Volume Conversion Table for Different Contrast Agents

| | OMNIPAQUE 300 | VISIPAQUE 270 | ISOVUE 370 |
| --- | --- | --- | --- |
| OMNIPAQUE ® 300 | 1 | 1.1161 | 0.8138 |
| VISIPAQUE ® 270 | 0.896 | 1 | 0.7291 |
| ISOVUE ® 370 | 1.2288 | 1.3715 | 1 |

This written description uses examples to disclose the present subject matter, including the best mode, and also to enable any person skilled in the art to practice the present approaches, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method of image processing, comprising executing with a processor the steps of:
generating a simulated first monochromatic contrast-enhanced X-ray image at a first energy and a simulated second monochromatic contrast-enhanced X-ray image at a second energy, wherein the first and second energies are different, and wherein the simulated first and second monochromatic contrast-enhanced X-ray images are simulated from a first polychromatic contrast-enhanced X-ray image at a first peak energy and second polychromatic contrast-enhanced X-ray image at a second peak energy, respectively, wherein the first and second peak energies are different;
isolating a first region of enhanced contrast from the first monochromatic contrast-enhanced X-ray image and a second region of enhanced contrast from the second monochromatic contrast-enhanced image, wherein the first and second regions of enhanced contrast comprise a partial signal attributable to a contrast agent from the simulated first monochromatic contrast-enhanced X-ray image and the simulated second monochromatic contrast-enhanced X-ray image;
determining an amount of the contrast agent within first and second regions of enhanced contrast based at least on a derived partial signal attributable to the contrast agent and respective signal responses of the simulated first and second monochromatic contrast-enhanced X-ray images;
generating a contrast agent density map over the first and second regions of enhanced contrast using the determined amount of contrast agent; and
outputting the contrast agent density map on a display coupled to the processor.

2. The method of claim 1, wherein the first and second regions of enhanced contrast comprise at least one blood vessel having a mixture of blood and the contrast agent.

3. The method of claim 2, further comprising determining a contrast agent volume occupied by the contrast agent within a given volume in the first and second regions of enhanced contrast based at least on respective linear attenuation coefficients of the contrast agent, the blood, and the given volume at the first and second energies.

4. The method of claim 3, wherein determining the amount of the contrast agent is further based on the determined contrast agent volume.

5. The method of claim 4, further comprising determining a contrast agent density using the amount of the contrast agent and the given volume.

6. The method of claim 5, wherein generating the contrast agent density map is further based on the determined contrast agent density.

7. The method of claim 1, further comprising using the processor to derive the partial signal attributable to the contrast agent by modeling an output of one or more equations relating the volume occupied by the contrast agent within a given volume in the first and second regions of enhanced contrast to a relationship between the respective spectral responses of the simulated first and second monochromatic contrast-enhanced X-ray images.

8. The method of claim 7, wherein the relationship between the respective spectral responses of the simulated first and second monochromatic contrast-enhanced X-ray images is represented by a Cartesian plot.

9. The method of claim 8, wherein the one or more equations relate the volume occupied by the contrast agent to a distance between a position on the Cartesian plot defined by a spectral response of the simulated first monochromatic contrast-enhanced X-ray image as an X value and a spectral response of the simulated second monochromatic contrast-enhanced X-ray image as a Y value and the origin of the Cartesian plot, wherein the origin is representative of the spectral response of water at the first and second energies.

10. The method of claim 8, wherein the one or more equations relate the volume occupied by the contrast agent to an angle between a line drawn to a position on the Cartesian plot from the origin and the X-axis of the Cartesian plot, wherein the position is defined by a spectral response of the simulated first monochromatic contrast-enhanced X-ray image as an X value and a spectral response of the simulated second monochromatic contrast-enhanced X-ray image as a Y value and the origin of the Cartesian plot, wherein the origin is representative of the spectral response of water at the first and second energies.

11. The method of claim 1, wherein the contrast agent comprises an element of interest, and wherein determining the amount of the contrast agent comprises determining an amount of the element of interest.

12. The method of claim 1, wherein generating the simulated first and second monochromatic contrast-enhanced X-ray images comprises performing X-ray spectral imaging at the first and second energies, respectively, on the first polychromatic contrast-enhanced X-ray image obtained at the first peak energy and the second polychromatic contrast-enhanced X-ray image obtained at the second peak energy.

* * * * *